United States Patent [19]

Ling et al.

[11] Patent Number: 4,837,306
[45] Date of Patent: Jun. 6, 1989

[54] METHOD FOR SELECTING HYBRIDOMAS PRODUCING ANTIBODIES SPECIFIC TO THE P-GLYCOPROTEIN CELL SUFACE ANTIGEN AND A CDNA CLONE ENCODING THE C-TERMINAL PORTION OF THE ANTIGEN

[75] Inventors: Victor Ling, Toronto; Norbert Kartner, Ajax, both of Canada

[73] Assignee: The Ontario Cancer Institute, Toronto, Canada

[21] Appl. No.: 930,390

[22] Filed: Nov. 10, 1986

Related U.S. Application Data

[63] Continuation-in-part of Ser. No. 705,361, Feb. 25, 1985, abandoned.

[51] Int. Cl.$^4$ .................... C07K 15/14; G01N 33/577
[52] U.S. Cl. .................... 530/387; 435/172.2; 435/240.27; 435/948; 436/548; 436/813; 530/808; 935/90; 935/104
[58] Field of Search ................. 435/172.2, 240.27, 948; 436/548, 813; 530/387, 808; 935/90, 104

[56] References Cited

PUBLICATIONS

F. B. Armstrong, *Biochemistry*, 2nd Ed., Oxford University Press, New York, 1983, pp. 218–219.
C. A. Molinaro et al., in R. M. Nakamura et al (Eds.), *Immunologic Analysis*, Masson Publishing, U.S.A., New York, 1982, pp. 129–143.
C. J. O'Hara et al., *Immunology Letters*, 5, 15–18, 1982.
C. J. O'Hara et al., *Journ. Clin. Immunol.*, 4, 403–441, 1984.
J. R. Riordan et al., *Journ. Biol. Chem.*, 254, 12701–12705, 1979.
C. J. O'Hara; Characterization of Monoclonal Antibodies Demonstrating Specificity for Drug-Resistant Tumour Cells; PhD. Thesis Sep., 1983; pp. 5.1–5.5

*Primary Examiner*—Sam Rosen
*Assistant Examiner*—David A. Saunders
*Attorney, Agent, or Firm*—Ridout & Maybee

[57] ABSTRACT

The invention provides a method for selecting hybridomas which produce antibodies specific to domains of a cell surface antigen which is usually not accessible at the surface of intact cells. The method employs the screening of the hybridoma clones obtained for the production of antibodies specific against the cell surface antigen by use of immunoblotting analysis, namely by screening the clones against antigen immobilized on a solid substrate such as nitrocellulose. The invention also includes those hybridomas and monoclonal antibodies when produced according to the method. The method provides monoclonal antibodies to P-glycoprotein surface antigen correlated with multidrug resistance. The antibodies are used to obtain a cDNA probe which in turn was used to select a cDNA clone encoding for a portion of the P-glycoprotein including the C-terminal end. The C-terminal portion of the P-glycoprotein comprising about 239 amino acids and localized to the cytoplasmic side of the plasma membrane contains the epitopes for binding of the monoclonal antibodies.

6 Claims, 9 Drawing Sheets

|               |         |                           |
|---------------|---------|---------------------------|
| oppD-protein  | 40-63   | L N F T L R A G E T L G I V G E S G S G K S T L |
| malK-protein  | 22-45   | I N L D I H E G E F V V F V G P S G C G K S T L |
| pstB-protein  | 29-52   | I N L D I A K N Q V T A F I G P S G C G K S T F |
| hisP-protein  | 25-48   | V S L Q A R A G D V I S I I G S S G S G K S T F |
| hlyB-protein  | 488-511 | I N L S I K Q G E V I G I V G R S G S G K S T L |
| P-glycoprotein| 218-241*| L N L E V K K G Q T L A L V G S S G C G K S T V |
| consensus     |         | h N L h G h h G S G G K S T |
| adenylate kinase |      | M L K K G G K T |
| p21 protein (H-ras-1) |  | - - - - L V V G G G K S |
| biotin carboxyl carrier | | F A A G G G K |
| ATPase - beta chain |    | L F K G L F G G G K - T V |
| ATPase - alpha chain |   | I G Q I I G G K - T |

|               |         |                                                                       |
|---------------|---------|-----------------------------------------------------------------------|
| oppD-protein  | 164-202 | P H E F S G G M R Q R V M T A M A L L C R P K L L I A D E P T T A L D V I V Q |
| malK-protein  | 131-169 | P K A L S G G Q R Q R V A I G R T L V A E P S V F L L D E P L S N L D A A L R |
| pstB-protein  | 151-189 | G Y S L S G G Q Q Q R L C I A R G I A I R P E V L L L D E P C S A L D P I S T |
| hisP-protein  | 151-189 | P V H L S G G Q Q Q R V S I A R A L A M E P D V L L F D E P T S A L D P E L V |
| hlyB-protein  | 603-641 | G A G L S G G Q R Q R I A I A R A L V N P K L I I F D E A T S A L D Y E S E |
| P-glycoprotein| 335-373*| G I Q I S G G Q K Q R I A I A R A L V R Q P H I L L L D E A T S A I D I E S E |
| consensus     |         | L S G G Q Q R h I A R L h P h h h h D E S A L D |
| adenylate kinase |      | R - I Q P L L L Y V D A |
| p21 protein (H-ras-1) |  | L L D I L D T A |
| biotin carboxyl carrier | | A Q V L V L E A |
| ATPase - beta chain |    | R - V L L F V D |
| ATPase - alpha chain |   | R - A L I I Y D D |

FIG. 10

METHOD FOR SELECTING HYBRIDOMAS PRODUCING ANTIBODIES SPECIFIC TO THE P-GLYCOPROTEIN CELL SUFACE ANTIGEN AND A CDNA CLONE ENCODING THE C-TERMINAL PORTION OF THE ANTIGEN

This application is a continuation-in-part of ser. no. 705,361 filed Feb. 25, 1985, now abandoned.

The present invention relates to a method for selecting hybridomas (i.e. immortal clones) which produce antibodies specific to domains of a surface antigen which is usually not accessible at the surface of intact cells, and in particular to the P-glycoprotein surface antigen correlated with multidrug resistance (Juliano, R. L. & Ling, V. Biochem. Biophys. Acta 455, 152–162 (1976)). The invention also relates to such hybridomas and the monoclonal antibodies they produce.

Clinical resistance to combination chemotherapy poses a major obstacle to the successful treatment of neoplastic disease such as cancer. The underlying mechanisms of such clinical resistance are largely unknown. No diagnostic reagents are currently available to define the nature and degree of resistance in a patient, and thereby facilitate a rational choice of treatment, or provide a basis for more accurate prognosis. Numerous investigators have developed mammalian tissue culture and in vivo models of tumours resistant to diverse drugs in the hope of gaining insights into the mechanisms of clinical resistance to combination chemotherapy. Significantly, these models have a number of features in common which define what is now termed the multidrug resistance phenotype (Kartner, N., Riordan, J. R. & Ling, V. Science 221, 1285–1288 (1983); and Ling, V., Gerlach, J. & Kartner, N. Breast Cancer Res. Treat. 4, 89–94 (1984)). These features include (i) a pleiotropic cross-resistance to unrelated drugs, (ii) reduced net accumulation of the drugs involved, and (iii) the anomalous expression of a 170,000 dalton cell surface component, the P-glycoprotein. Other observations have also been noted in different cell lines, but qualitatively only the above features of multidrug resistance have remained consistent regardless of the initial drug of selection, or the mammalian species under investigation.

The striking correlation between P-glycoprotein expression and the expression of the multidrug resistance phenotype raises the possibility that P-glycoprotein might serve as a diagnostic marker for the detection of multidrug-resistant malignant cells in cancer patients. Also, because the P-glycoprotein is found in different mammalian species, it probably plays an important functional role in the mammalian cell surface. What this role might be in multidrug-resistant cells, or in normal tissue, is not yet understood.

An objective of the invention was to obtain monoclonal antibodies that would serve as versatile analytical reagents, preferably recognizing homologous regions of the P-glycoproteins of different species. For this reason, in designing a strategy for selecting monoclonal antibodies specific for P-glycoprotein, several theoretical considerations were taken into account. Firstly, P-glycoprotein bears a carbohydrate moiety which may account for 20–30% of its molecular size (Ling, V., Kartner, N., Sudo, T., Siminovitch, L. & Riordan, J. R. Cancer Treat. Rep. 67, 869–874 (1983)). The extracellular domain of the polypeptide moiety appears to be either very limited, or sequestered by the relatively large carbohydrate moiety. Thus, conserved antigenic sites of P-glycoprotein, which are presumably associated with the polypeptide moiety, may not be accessible on the cell surface. Secondly, in other systems, selections based on binding to the cell surface have often yielded antibodies directed toward carbohydrate determinants of glycoconjugates. Such determinants vary with stage of differentiation and oncogenic transformation, and they may be common to different glycoproteins and glycolipids. Furthermore, the changes that occur in their distribution in the unstable environment of the neoplastic cell remain unclear. Thus, antibodies directed toward carbohydrate determinants of P-glycoprotein, or other glycoprotein antigens, are of limited utility in defining the gene product to which the antigenic sites are attached. Thirdly, since there appears to be a basal level of P-glycoprotein expression in drug-sensitive cells, P-glycoprotein may be a normal component of the mammalian cell surface. It follows that there may be regulation against an immune response to the extracellular domain of P-glycoprotein if it is recognized as a self antigen. Fourthly, it has been observed that monoclonal antibodies toward native proteins are often poor reagents for immunoprecipitation and immunoblotting analysis. This is a particularly important problem when considering membrane components, which are often denatured during analytical procedures. It would be difficult to determine precisely the identity of the antigen to which an antibody bears specificity, without the advantages of immunoprecipitation or immunoblotting analysis. Finally, we were aware that although attempts have been made to prepare P-glycoprotein specific monoclonal antibodies, using cell surface binding as a criterion for selection, these have failed, so far, to produce generally useful reagents proven to be directed against P-glycoprotein (O'Hara, C. J. & Price, G. B. Immunol. Lett. 5, 15–18 (1982); and Sugimoto, Y., Suzuki, H. & Tanaka, N. Biochem. Biophys. Res. Comm. 114, 969–975 (1983)).

Because of these theoretical considerations, a screening method for immortal clones (hereinafter also referred to as hybridomas) was designed that would avoid relying on a cell surface binding assay, and that would guarantee the selection of monoclonal antibodies which would serve as useful reagents for immunoblotting.

Accordingly, the invention provides a method for selecting immortal clones which produce antibodies specific to domains of a cell surface antigen which is usually not accessible at the surface of intact cells, comprising the steps of: immunizing a suitable mammal with cell or tissue fractions containing plasma membranes of a mammalian cell line of interest; immortalizing antibody producing cells from said immunized mammal to form a plurality of immortal antibody producing clones; and screening said clones for production of antibodies specific against said antigen immobilized on a solid substrate.

The invention also provides hybridomas which produce antibodies, i.e. monoclonal antibodies, specific for such cell surface antigens, and particularly P-glycoprotein, as well as such monoclonal antibodies themselves when such hybridomas and monoclonal antibodies are produced by the aforesaid method of the invention.

P-glycoprotein appears to be highly conserved among mammalian species. Monoclonal antibodies of the present invention which bind to Chinese hamster ovary (CHO) P-glycoprotein cross-react with P-glycoprotein from other rodent or human multidrugresistant cell lines. This conservation extends to the DNA level. A 640 bp cDNA clone (pCHP1), which encodes the C-terminal region of CHO P-glycoprotein, hybridizes strongly to mouse and human DNA. This probe has been used to select for other longer P-glycoprotein cDNA clones (e.g. pL28) of about 2,000 bp from CHO cells. This probe has also been used to localize the human P-glycoprotein genes to chromosome 7q36. The complex pattern of restriction fragments detected by the pCHP1 probe in Southern blot analyses of DNA from human, hamster and mouse cell lines suggests that P-glycoprotein is encoded by a multigene family. Amplification of the P-glycoprotein genes, resulting in increased expression of P-glycoprotein, is often observed in multidrugresistant cell lines. The differential amplification of P-glycoprotein genes observed in some multidrug-resistant cell lines raises the possibility that differential expression of P-glycoprotein may contribute to the overall multidrug resistance phenotype.

The actual function of P-glycoprotein in multidrug resistance is not understood. The basis of resistance appears to be a reduced cellular drug accumulation. Thus, it has been speculated that P-glycoprotein directly or indirectly mediates either the influx or efflux (or both) of drugs across the plasma membrane. The present invention provides the amino acid sequence of P-glycoprotein which has provided significant insights into the function of P-glycoprotein. The striking homology between P-glycoprotein and the hemolysin B (hlyB) protein of E. coli, together with the parallels between multidrug resistance and the export of alpha hemolysin, has resulted in the proposition of a model that provides a direct role for P-glycoprotein in mediating multidrug resistance.

A BRIEF DESCRIPTION OF THE DRAWINGS

FIG. 2 shows in panel A, dot immunoblots using antibodies from eight cloned hybridomas against plasma membranes from both drug sensitive and resistant cells, and panel B shows monoclonal antibody staining of plasma membranes of drug-resistant and sensitive cells.

FIG. 3 shows graphic analyses of direct competitive binding assay of eight monoclonal antibodies against purified, radioiodinated antibody.

FIG. 6 shows the relationship between the pL28 and pCHP1 cDNA clones of P-glycoprotein. The boxed area in pL28 identifies an 1323 bp open reading frame. The unhatched area in the box is a putative transmembrane region and the hatched area is the region exhibiting homology with the C-terminus of the hemolysin B (hlyB) protein.

FIG. 7 shows the nucleotide sequence of the clone pL28 including an open reading frame of 1323 bp and the deduced amino acid sequence corresponding thereto, the clone pCHP1 is shown in the boxed region.

FIG. 9 shows aligned sequences of the C-terminal 239 amino acids of P-glycoprotein (upper sequence) and the C-terminal 236 amino acids of the hemolysin B (hlyB) protein (lower sequence). Conserved amino acid substitutions (defined by scores greater than zero in the mutation probability data matrix for amino acid replacements) are boxed with amino acids identical in both sequences indicated by stars (***). Three single amino acid gaps introduced for alignment (following position 215 in the pL28 sequence and positions 566 and 577 in the hlyB sequence) are indicated by dashes (—). The underlined regions (A—A and B—B) contain the highly conserved nucleotide-binding sites and are shown aligned with other nucleotide-binding proteins in FIG. 10.

Figure 1:
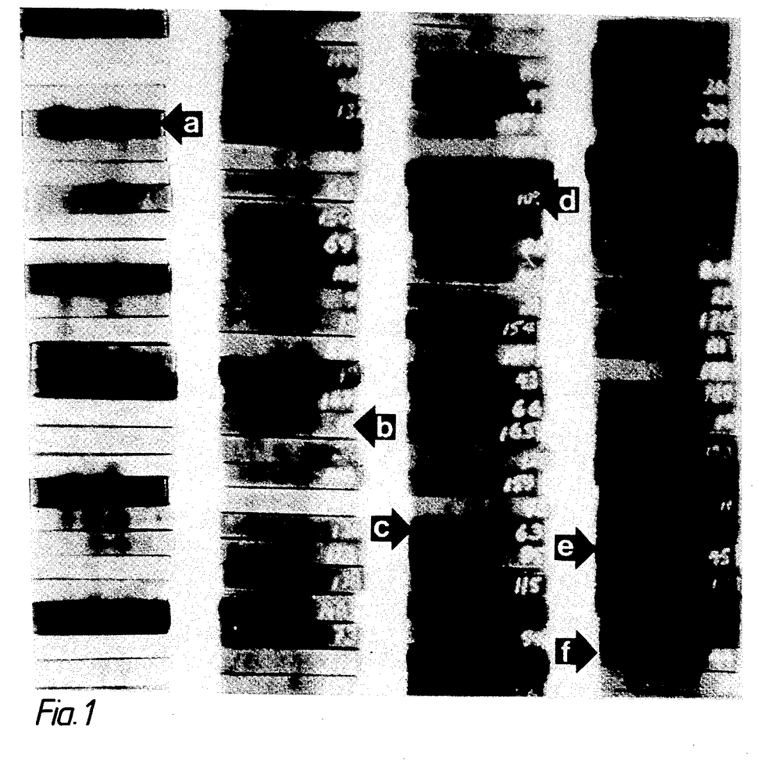
FIG. 1 shows examples of dot immunoblots used in the screening of hybridomas made in accordance to the invention.

In the preferred method of the invention, mice were immunized with sodium dodecyl sulphate (SDS)-solubilized plasma membranes of multidrug-resistant Chinese hamster ovary (CHO) and human cell lines. Hybridomas were formed from spleen cells taken from the mice by fusion with a suitable fusion partner (see Example 1 below). Using a cross-species panel of detergent-solubilized plasma membranes immobilized on nitrocellulose filter test strips, it was ensured that the monoclonal antibodies selected would bind to conserved, drug resistance-specific epitopes in the denatured antigen, as they would be presented in protein immunoblots (Western blots) after SDS-polyacrylamide gel electrophoresis (SDS-PAGE). Results of a hybridoma screening, using nitrocellulose test strips, are shown in FIG. 1. As expected, a number of different specificities were observed, including those toward common mammalian, CHO or human antigens (FIG. 1: f, e and c, respectively). More importantly, specificities toward membranes of resistant cell lines, either CHO or human, or both, were observed (FIG. 1: b, d and a, respectively). The majority of strips are negative or only weakly stained. Specificities other than those indicated in FIG. 1 were only rarely seen and generally did not breed true. Primary screening of hybridoma supernatants of 1,007 wells which were positive for growth yielded 71 wells positive for drug resistant cell membrane (19 against human only, 37 against CHO only, and 15 against both). After expansion of these wells and secondary screening, 21 strongly positive wells remained (2 against human only, 5 against CHO only, and 14 against both). Hybridomas specific for drug resistant membranes were cloned twice by limiting dilution, using the above screening method to select specific antibody-producing clones. Eight stable clones were ultimately isolated (3 against CHO only, and 5 against both CHO and human). Losses of specific antibody secreting hybrids were presumably due to their genetic instability. The primary screening results probably reflect the presence of an initial population of unstable specific antibodyproducing hybrids, rather than a large proportion of false positives. All further characterization was accomplished using the final, twice-cloned hybridomas.

Characterization of Monoclonal Antibodies

The results of the initial screening of the hybridomas clearly indicate that some differences in the binding sites recognized by the different antibodies are to be expected. For example, three of the eight final clones showed no affinity for membranes of drug-resistant human cells. In order to characterize these differences more precisely, supernatants from cloned hybridomas were screened with a larger panel of drug-sensitive and resistant plasma membranes. Test strips were also prepared for immunoblotting plasma membranes of sensitive and resistant CHO cells after SDS-PAGE. FIG. 2 (A and B) shows the results of these experiments. In FIG. 2(A) the results of dot blotting a larger panel of cell lines allows the classification of the eight monoclonal antibodies into three distinct groups (I, II and III) according to the pattern of staining obtained. No significant staining of drug-sensitive cell membranes was observed for any cell line, with any of the eight monoclonal antibodies. The monoclonal antibodies in Group I appear to stain all drug-resistant membranes tested. Those of Group II stain drug-resistant CHO and mouse membranes, but stain human membranes only very poorly. The single member of Group III stains drug-resistant CHO and human membranes, but not those of mouse. Other minor differences are also observed among the three groups.

In order to determine the molecular sizes of the antigens being stained by the monoclonal antibodies, Western blots of drug-sensitive and drug-resistant plasma membranes were overlayed with hybridoma supernatants and developed using a radiolabelled second antibody. As shown in FIG. 2(B), all of the antibodies stained a major drug-resistance specific band of approximately 170,000 daltons. It is of interest that faint bands of lower molecular weight are also stained. These bands are variable among different preparations of plasma membranes from the same cells, and may be proteolytic fragments of the major staining band. None of these minor bands are observed in membranes of drug-sensitive cells. Similar putative breakdown products have been described previously, when using polyclonal rabbit antisera specific for P-glycoprotein of multidrug-resistant plasma membranes (Kartner, N., Riordan, J. R. & Ling, V. *Science* 221, 1285-1288 (1983)). Activation of membrane-associated proteases during detergent solubilization, or chemical cleavage of proteins during heating in the presence of SDS are common phenomena. Niman and Elder, for example, have described in detail the natural breakdown fragments of the murine retroviral envelope glycoprotein, gp70, and have used these fragments in a general scheme for mapping the antigenic sites of gp70 (Niman, H. L. & Elder, J. H. in *Monoclonal Antibodies and T Cell Products* (ed Katz, D. H.) 23-51 (CRC Press, Boca Raton, Florida, 1982)). In this context, it is of interest that when a single plasma membrane preparation was probed with different monoclonal antibodies, two different patterns of low molecular weight bands were seen. FIG. 2(B) shows the patterns obtained with representative antibodies of Groups I, II and III. Group I antibodies yielded one pattern, whereas Groups II and III yielded a different pattern. This suggests that a natural proteolytic cleavage site may separate the Group I epitope from the Groups II and III epitopes. Any attempt at mapping the epitopes more precisely, without additional information, may be complicated by the possibility that epitopes could be repeated within the P-glycoprotein polypeptide, or could be present on different members of a family of similar, but not identical P-glycoproteins.

Differences in the peptide maps and in the staining patterns against a panel of different plasma membranes suggest that there may be three different antigenic sites. To provide more direct evidence of differences among the eight monoclonal antibodies and to determine the spatial relationships of their binding sites, competitive binding studies were performed with ascites of the different hybridomas and purified, radio labelled representatives of the three antibody groups. Typical competition assay results are shown in FIG. 3. These results clearly allow the classification of the antibodies into three groups (I, II and III) on the basis of their binding to three spatially distinct epitopes.

In the direct competitive binding assay of eight monoclonal antibodies against purified, radioiodinated antibody shown in FIG. 3, the target antigen was plasma membrane vesicles from $CH^RB30$, immobilized on nitrocellulose in 96-well plates. The abscissa in FIG. 3 is logarithmic scale of concentration ratio of unlabelled competing antibody to radiolabelled antibody. The ordinate is percent scale of cpm bound, normalized to cpm bound in the absence of competing antibody. Results of single simultaneous experiments are shown for clarity. Panel I shows competition of a labelled Group I antibody (C219) with dilutions of ascites fluids containing antibodies generated by the eight different hybridomas. No Group II or Group III antibodies compete with C219. The shift in competition curves of other Group I antibodies with respect to the self-competition curve of C219 probably reflects differences in binding avidity. Errors in quantitation of antibodies of different isotypes may also contribute to an apparent shift. Panel II shows competition of Group II antibody (C32) with other ascites fluids. Group I and III antibodies do not compete with C32. Binding kinetics of the three Group II antibodies appear to be very similar. Panel III displays the competition data for the single representative of Group III (C494). No Group I or Group II antibodies compete with C494. Antibodies tested were C11, ; C26, C32, ; C36, ; C103, ; C219, ; C494, ; and C699, .

Specific Detection of P-Glycoprotein

Figure 4:
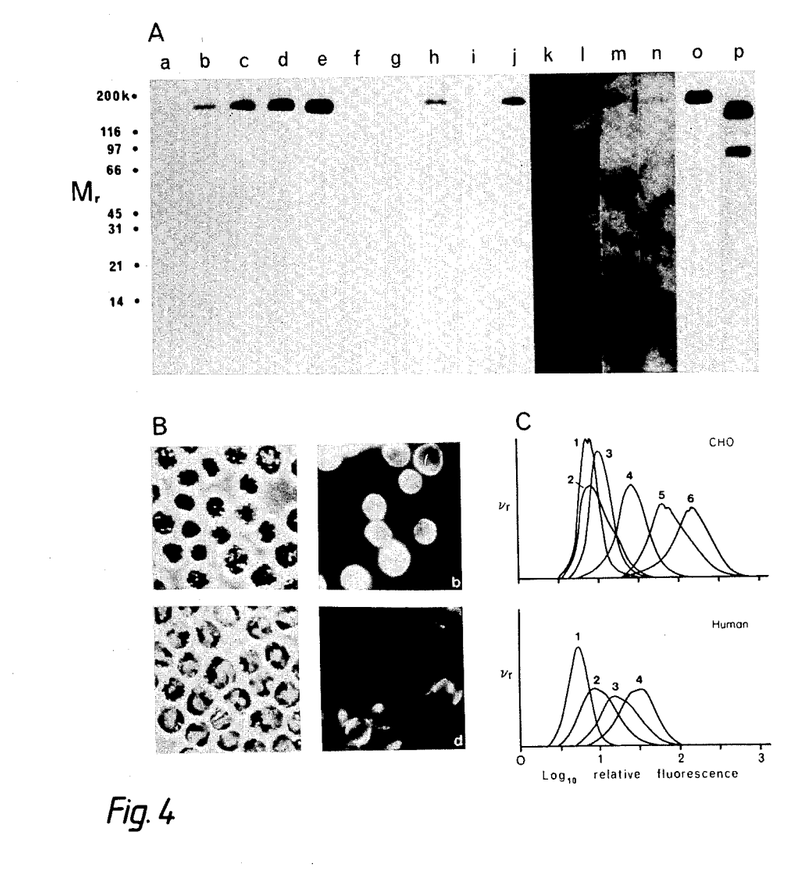
FIG. 4 shows in panel A, Western blots of plasma membranes of drug sensitive and resistant cells using monoclonal antibody; in panel B indirect immunofluorescence staining of drug-resistant cell with monoclonal antibody; and in panel C flow cytometry of indirect immunofluorescence staining using cell lines of different drug resistance.

The evidence presented above strongly suggests that the monoclonal antibodies under investigation bind the P-glycoprotein of multidrug resistant cells, but this conclusion needs to be corroborated by testing the antibodies on cell lines which have been used previously to define the P-glycoprotein. Although dot blots have shown differential staining of drug-resistant cell membranes, it is not clear that the same antigen is bound in each case. Previous work has shown that homologous P-glycoproteins of consistent molecular weight are expressed in all multidrug resistant cell lines so far tested (Kartner et al. *Science*, supra,; Giavazzi, R., Kartner, N. & Hart, I. R. *Cancer Chemother. Pharmacol.* 13, 145-147 (1984); Kartner, N., Shales, M., Riordan, J. R. & Ling, V. *Cancer Res.* 43, 4413-4419 (1983)). Thus, Western blots of a series of plasma membranes were stained, using radioiodinated monoclonal antibody. FIG. 4(A) shows the results of staining a series of plasma membranes from CHO cells of increasing colchicine resistance, and a drug-sensitive revertant (lanes a-d, and f). A daunorubicin resistant CHO cell line was also tested (lane e). Furthermore, blots of colchicine resistant mouse (lane h) and vinblastine resistant human cells (lane j) were probed (compare with drug sensitive parental cells, lane g and i, respectively). Longer exposure of the blots (lanes k-n) reveals faint bands in the membranes of sensitive parents and revertant cells in lanes a, f, g and i respectively. Low level expression of P-glycoprotein in drug-sensitive cells has been reported previously (Kartner et al. *Science*, supra). Trivial explanations for the apparent homologies of the 170k bands in different species, such as detection of phosphate or common carbohydrate epitopes are ruled out by the controls in lanes o and p. The correlation of increasing P-glycoprotein expression with increasing multidrug resistance and the conservation of the antigen molecular size regardless of the drug of selection in a number of mammalian species confirm that the antigen bound by the monoclonal antibodies is P-glycoprotein as it has been previously defined (Kartner et al. *Science*, supra).

The foregoing demonstrates that detergent-solubilized and denatured P-glycoprotein immobilized on nitrocellulose filters is detected with the monoclonal antibodies under study. In many applications for diagnostic or research purposes it is important that an antibody be capable of detecting the antigenic site as it is presented in intact cells and tissues. In this regard it has been found, using both radiolabelled antibody and indirect, immunofluorescence staining, that none of the monoclonal antibodies binds the surface of intact multidrug resistant cells. Nonetheless, as is seen in FIG. 4(B), using fixed and permeabilized cells, the monoclonal antibodies are capable of labelling the surface membrane of resistant CHO and human cells. It is apparent from this work that the epitopes defined by the monoclonal antibodies are either cryptic, or exposed on the cytoplasmic face of the plasma membrane. When native plasma membrane vesicles are spotted onto nitrocellulose, all eight antibodies bind to them at least as well as to SDS solubilized membranes, showing that protein unfolding is probably not a requisite for epitope recognition. It is presumed therefore, that the antibodies bind the exposed cytoplasmic domain of relatively native P-glycoprotein in disrupted, or inside-out membrane vesicles. FIG. 4(C) demonstrates that with the use of flow cytometry the degree of staining of cells with these monoclonal antibodies can be determined semi-quantitatively and correlates with the degree of drug resistance of the cells. Such a relationship exists between the degree of drug resistance and the amount of P-glycoprotein expressed in drug-resistant cells, (Kartner et al. *Science*, supra; Kartner et at. *Cancer Res.*, supra, Giavazzi et al. *Cancer Chemother Pharmacal*, supra; Riordan, J. R., and Ling, V. *J. Biol. Chem.* 254, 12701-12705 (1979)).

This same correlation, which is obtained between fluorescence intensity and the degree of drug resistance of the resistant cells shown in FIG. 4(C), is strong corroborative evidence that P-glycoprotein is being stained specifically. Furthermore, FIG. 4(B and C) demonstrates that these monoclonal antibodies are indeed useful as reagents for the staining of cells and tissues. In addition to their use in indirect immunofluorescence methods, the antibodies have been used in conventional immunoperoxidase staining techniques.

LOCALIZATION OF THREE EPITOPES TO A CONSERVED DOMAIN OF P-GLYCOPROTEIN

Figure 5:
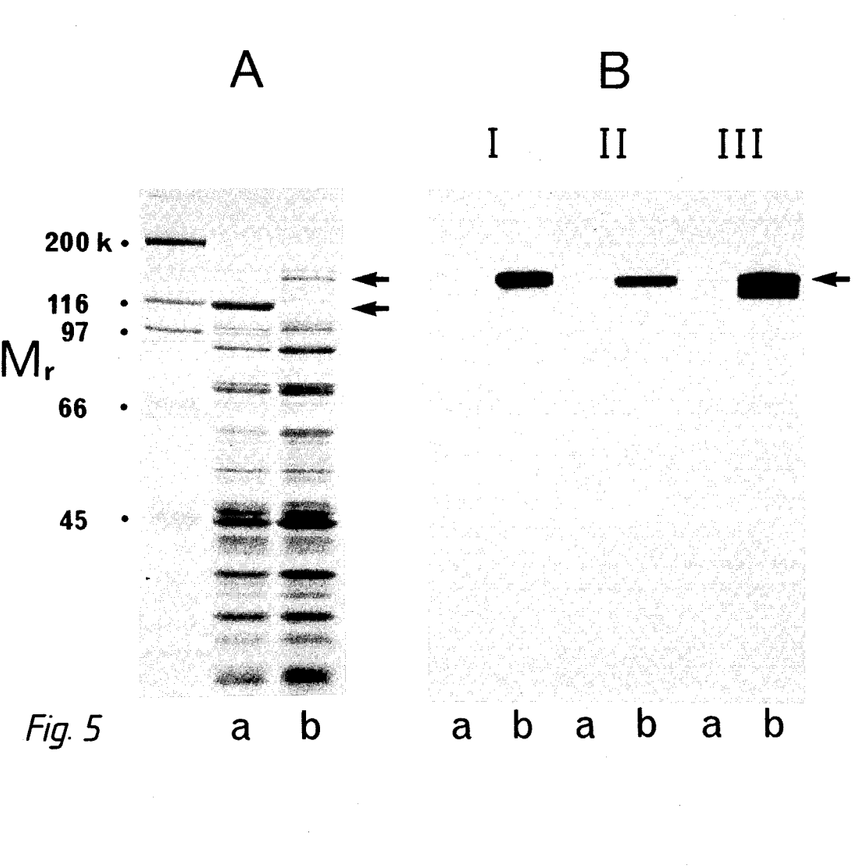
FIG. 5 shows probing of pCHP1 lacZ fusion product containing a P-glycoprotein peptide fragment with different monoclonal antibodies.

The Group I monoclonal antibody, C219, has been used to obtain a 640 bp cDNA probe, pCHP1, from a λgt11 expression library of the multidrug-resistant CHO cell line, CH$^R$B30. The lacZ fusion product of pCHP1 presumably includes the epitope which is bound by C219. Independent evidence, including resistance associated gene amplification in Southern blots of genomic DNA probed with pCHP1, strongly supports the notion that the cDNA codes for a fragment of P-glycoprotein, presumably in the region of its C-terminus. For a number of reasons, it is of interest to know whether the antibodies recognizing different epitopes bind the same lacZ fusion product. Firstly, the existence of more than one epitope on the pCHP1-coded polypeptide would provide very strong corroborative evidence that the cDNA does indeed encode a fragment of the P-glycoprotein. Although a single P-glycoprotein specific monoclonal antibody could possibly bind a non-P-glycoprotein antigen, it is unlikely that antibodies binding independent epitopes would bind the same non-P-glycoprotein antigen. Secondly, peptide fragments such as that encoded by pCHP1 could serve as reagents for determining additional subgroups among the groups of monoclonal antibodies that bind to the lacZ fusion product. Finally, binding data would allow a crude localization of the different epitopes, possibly providing some insights into the structure of the P-glycoprotein. In FIG. 5(A) lysates of control λgt11-infected bacteria and pCHP1-infected bacteria have been resolved by SDS-PAGE. In the control lysate (lane a) a heavy B-galactosidase band is seen. In the pCHP1 lysate this band has disappeared and a major lacZ fusion band is seen at about 145,00 daltons. This band is approximately of the size expected if most, or all, of the pCHP1 insert encodes an open reading frame. Numerous new bands of somewhat lower molecular weight than the major lacZ fusion band are also seen. These are presumably proteolytic fragments of the lacZ fusion product. FIG. 5(B) shows the results of probing Western blots of the lacZ fusion product of pCHP1 with monoclonal antibodies of each of the three groups. All three epitopes are detected in the same polypeptide fragment. Although the Groups I and II antibodies appear to stain only the major lacZ fusion product band, the Group III antibody stains many of the lower molecular weight fragments as well. Since the lower molecular weight bands are all larger than B-galactosidase, and the insert-encoded peptide is attached to the C-terminus of B-galactosidase, crude mapping of the epitopes is possible. The staining of the putative proteolytic fragments suggests that the Group III epitope is distal from the C-terminus of the pCHP1 encoded peptide. Since only the major, or largest, bands appear to be stained by the Groups I and II antibodies, it is likely that they are clustered near the Cterminus of the peptide. Dot blots of pCHP1 lysates and control λgt11 lysates confirm that all eight monoclonal antibodies bind the lacZ fusion product. This is a surprising result, since pCHP1 probably encodes less than 20% of the P-glycoprotein polypeptide. The presence of three independent epitopes in the lacZ fusion product clearly confirms that pCHP1 codes for P-glycoprotein. Furthermore, this observation suggests than an immunogenic and conserved domain exists in the C-terminal region of the P-glycoprotein.

In summary, a strategy has been designed and employed to select for monoclonal antibodies that bind conserved, multidrug resistance-associated antigens after SDS denaturation and immobilization on nitrocellulose. The method of hybridoma screening used in the present work is a generally useful technique for producing monoclonal antibodies against cell surface antigens. It assures reagents that will be useful for identifying antigens in the powerful Western blotting technique. Furthermore, it avoids some of the possible problems associated with cell surface binding assays and, thus, provides a complementary alternative for hybridoma screening. The method also provides a means of generating antibodies to cytoplasmic domains of membrane antigens. These domains are of great interest because of their functional association with the cytoplasm of the cell, and they have, as yet, rarely been characterized in detail.

In the production of monoclonal antibodies that differentially bind plasma membranes of multidrug resistance cells, eight different antibodies were obtained. It is significant that all eight antibodies show specificity toward the same antigen, the P-glycoprotein, supporting the notion that the expression of P-glycoprotein is the major alteration of the multidrug-resistant cell surface. Furthermore, each of the eight antibodies binds one of three distinct epitopes confined to a region less than 240 amino acids in length. This domain is apparently accessible only on the cytoplasmic surface of the plasma membrane and is presumably in the C-terminal region of the P-glycoprotein polypeptide.

It is interesting that three independent antigenic sites are clustered in this region. This suggests that the domain is relatively more immunogenic than the majority of the protein. Possibly this region represents a hydrophilic domain in an otherwise relatively hydrophobic protein. Alternatively, it has recently been suggested that regions of a polypeptide that are conformationally more fluid are more likely to be antigenic. Thus, the termini of polypeptides are often relatively antigenic regions. It is also of interest that no antibodies that bind an extracellular domain of the P-glycoprotein were obtained. The carbohydrate moiety, in particular, should be relatively unaffected by detergent solubilization and, for other glycoproteins, this moiety often accounts for a high proportion of antigenic sites. One explanation for the present observation is that carbohydrate determinants of P-glycoprotein might be common to other glycoconjugates, present in both drug-sensitive and drug resistant cells, and would not be detected in a differential screening assay. Alternatively, recognition of the extracellular domain of P-glycoprotein as a self-antigen, particularly if this domain is structurally conserved among mammalian species, could account for this observation.

The epitopes which have been defined in the cytoplasmic domain of the P-glycoprotein do not appear to be equally represented in different mammalian species. One of the epitopes described (Group I) is detected equally well in rodent and human P-glycoproteins and, therefore, appears to be highly conserved. The Group II epitope is detected in hamster, less well in mouse, and very poorly in human P-glycoprotein. This observation may reflect a species related structural divergence in this region of the protein. On the other hand, the Group III epitope is detected in hamster and less well in human P-glycoprotein, but very poorly in mouse. This epitope could represent a more variable region of P-glycoprotein structure. Another explanation might be that different members of a P-glycoprotein multigene family are expressed in different cell lines. This possibility as been previously proposed as a possible mechanism for variation in the cross-resistance patterns of multidrug resistant cells selected from common parental lines. The particular drug of selection, and possibly the characteristics of the parental cell line, may affect the amplification and overexpression of specific genes, or specific combinations of genes. Recently, Southern blot analysis of genomic DNA with a P-glycoprotein specific cDNA probe (pCHP1) has provided strong evidence in support of a multigene family of P-glycoproteins.

The antibodies described in the present work are the first molecular probes available for the assessment of the role of P-glycoprotein in human tumours and for the elucidation of the molecular biology of the multidrug resistance phenotype. Clinical application of the monoclonal antibodies for diagnosis of therapy-resistant disease is an obvious utility for this invention. Early detection of elevated levels of P-glycoprotein in tumours might indicate a departure from routine chemotherapy an application of novel treatments that may circumvent the multidrug resistance phenotype. Preliminary findings of elevated amounts of P-glycoprotein in some ovarian carcinomas of patients failing chemotherapy demonstrate the utility of the present monoclonal antibodies for this purpose. Furthermore, these reagents will be useful in the sensitive and specific detection of P-glycoprotein in experimental systems and in normal mammalian tissues. This will allow the study of the biosynthesis and functional role of P-glycoprotein in drug-resistant cells. Such studies will provide insights into structure and function at the mammalian cell surface, and also will establish a theoretical basis that might lead to improved chemotherapy of presently nonresponsive neoplastic disease.

EXAMPLE 1

Twelve week old (BALB/c×C3H)$F_1$ mice were immunized with injections of purified plasma membranes isolated according to Riordan and Ling (Riordan, J. R. & Ling, V. *J. Biol. Chem.* 254, 12701–12705 (1979)) from $CH^RB30$ and $CEM/VLB_{500}$ cell lines. Membrane protein was assayed according to a modification (Peterson, G. L. *Anal. Biochem.* 83, 346–356 (1977)) of the method of Lowry et al (Lowry, O.H., Rosebrough, N.J., Farr, A. L. & Randall, R. J. *J. Biol. Chem.* 193, 265–275 (1951)). Membranes were solubilized in a 2% SDS-containing buffer as for SDS-PAGE, with a protein:SDS ratio of 1:1.4, and were emulsified 1:1 with Freund's incomplete adjuvant. The first injection consisted of 200 μg of $CH^RB30$ membrane intraperitoneally, followed after 14 days by a second, identical injection. After 14 months the mice were injectefd with a mixture of 100 μg each of $CH^R30$ and $CEM/VLB_{500}$ plasma membranes. Identical injections were given 14 and 21 days after the first injection in this series. Additionally on day 21 a mixture containing 100 μg each of sonicated plasma membrane vesicles of $CH^RB30$ and $CEM/VLB_{500}$ was injected intravenously. On day 26 spleens were removed aseptially and splenocytes fused 3:1 with the Sp2/0-Ag14 fusion partner (Shulman, M., Wilde, C.D. & Kohler, G. *Nature* 276, 269-270 (1978)). Cells were plated in 96-well plates at $10^5$ myeloma cells per well in RPMI-1640 medium containing 100 µM hypoxanthine, 0.5 µM aminopterin, 30 µM thymidine, 2 mM L-glutamine 50 µM 2-mercaptoethanol and 15% fetal bovine serum. When wells appeared about one-quarter confluent (typically 50-80% of wells after 10-14 days), they were screened for specific antibody producing hybrids. Test strips were prepared by spotting 1 µl of SDS-solubilized plasma membrane (prepared as for SDS-PAGE) at 1 mg/ml concentration onto numbered 5 mm×25 mm nitrocellulose strips (see FIG. 1, Panel A). The dried dot blots were blocked in 3% bovine serum albumin (BSA)/saline for 1h at 37° and were placed into test tubes containing hybridoma supernatants diluted 1:10 in BSA/saline. After overnight incubation at 4° the strips were washed in several changes of PBS and were developed with $^{125}$I-labelled IgG goat anti-mouse immunoglobulins (Cappel; $10^6$ cpm/ml in 3% BSA/saline) for 6 h at 25°. After washing and drying, the test strips were taped to stiff plastic sheets and exposed overnight, with intensifying screens, on Kodak X-AR5 film at −70°. Typically about 1000 strips could be processed at the same time. Promising wells were expanded and cloned twice by limiting dilution. The above screening method was repeated to pick positive clones.

P-Glycoprotein cDNA Clones

The pCHP1 probe was used to select a cDNA clone (pL28) from an Okayama and Berg pcD vector-library prepared from a drug-sensitive Chinese hamster ovary cell line (the library construction and screening were as described in Elliott, E. M. et al, *G. Mol. Cell. Biol.*, 5, 236 (1985)). For DNA sequencing, the cloned insert was digested with BamHI and cloned into M13mp9. Both strands were sequenced using synthetic oligonucleotide primers and the dideoxy method of Sanger et al, *Proc. Natl. Acad. Sci. U.S.A.*, 74, 5463 (1977).

One such cDNA clone (pL28), which has been completely sequenced and contains the pCHP1 sequence, is illustrated diagrammatically in FIG. 6. Complete sequences are shown in FIG. 7 where the boxed region contains the sequence for pCHP1. The pL28 clone contains a 1323 bp open reading frame which ends with two successive termination codons and a 366 bp untranslated region which is followed by a poly(A) tail. While the nucleotide sequence of the open reading frame is similar to that in other cDNA clones, the untranslated regions differ suggesting that different members of the P-glycoprotein gene family are expressed in drug-sensitive cells.

Since the pCHP1 probe detects a mRNA of about 4.7 kb, the 441 amino acids encoded by pL28 represent about one third of the P-glycoprotein molecule. However, sequence data from overlapping clones indicate that the P-glycoprotein gene consists of a tandem duplication. Analysis of the amino acid sequence of pL28 and other cDNA clones, using the criteria of Eisenberg et al., *J. Mol. Biol.*, 179, 125 (1984), has identified 6 potential transmembrane segments in a region 5-prime of the pCHP1 homology (part of this region is indicated for pL28 by the open box in FIG. 6). The C-terminal 239 amino acids of P-glycoprotein (indicated by the hatched box in FIG. 6) have been localized to the cytoplasmic side of the plasma membrane by binding with fluorescein-labelled monoclonal antibodies.

Extensive Homology of P-Glycoprotein with the hlyB Protein

A search of the GenBank™ DNA Sequence Database (using the FASTN program from the National Biomedical Research Foundation (NBRF) Protein Identification Resource) detected extensive DNA sequence homology between pL28 and a gene required for hemolysin transport in E. coli, the hlyB gene. The four cistrons involved in the production and export of alpha hemolysin are: hlyA which encodes the hemolysin molecule (107 kd), hlyC, which encodes a small (20 kd) cytoplasmic protein which may be involved in processing hemolysin, and hlyB and hlyD (formerly $hlyB_a$ and $hlyB_b$) which encode membrane proteins required for the transport of hemolysin out of the bacterium. These genes, which can be located either on the bacterial chromosome or on plasmids, have been entirely sequenced (Felmlee, T. et al, *J. Bacteriol.*, 163, 94 (1985)).

Hemolysis is often associated with extraintestinal E. coli infections and is considered to be a virulence factor. The iron released by lysis of erythrocytes may give hemolytic strains a selective growth advantage over non-hemolytic *E. coli*. Alternatively, hemolysin may exert a cytotoxic effect on cells of the immune system.

Figure 8:
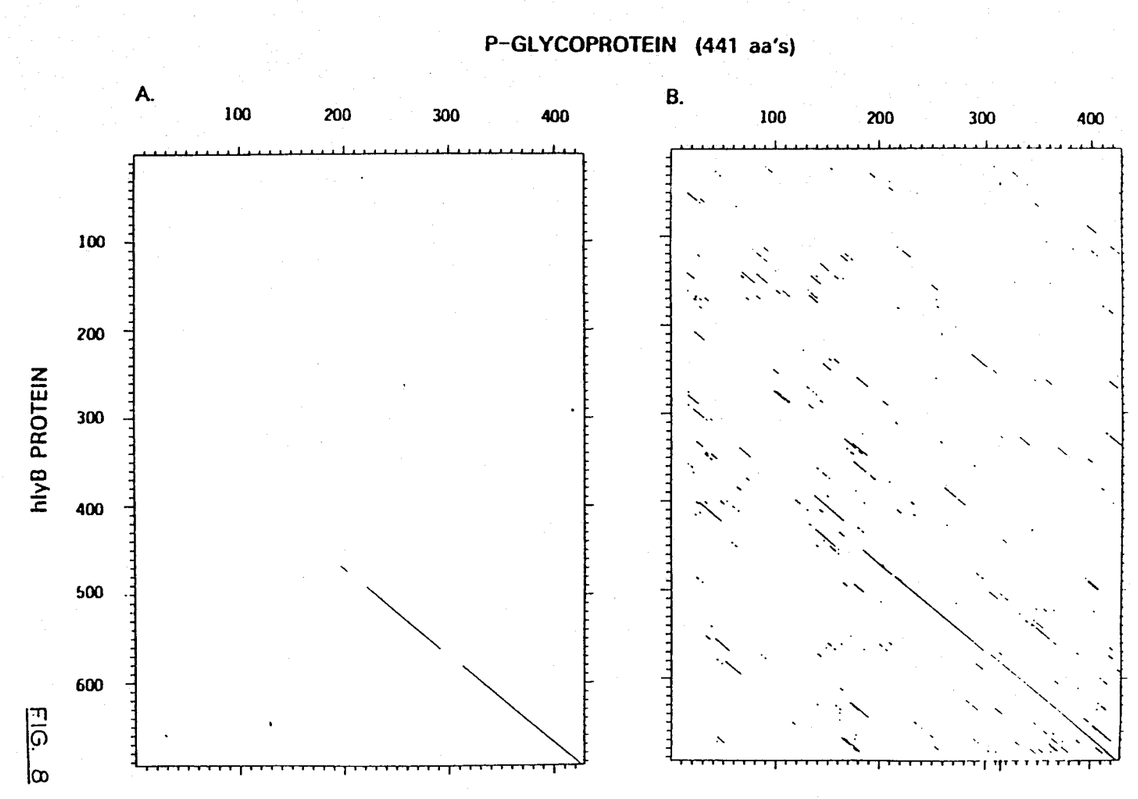
FIG. 8 shows a comparison of the C-terminal 441 amino acid sequence of P-glycoprotein and the 707 amino acid sequence of the hemolysin B (hlyB) protein. The plot was generated by the DOTMATRIX program from the National Biomedical Research Foundation Protein Identification Resource using the mutation probability data matrix for amino acid replacements for scoring. The window size was 30 amino acids and the minimum score required to generate a point was 40 in the high stringency plot (A) and 15 in the low stringency plot (B). Each minor division corresponds to 10 amino acids.

When the deduced amino acid sequence of the hlyB gene and pL28 were compared, the extensive C-terminal homology between P-glycoprotein and the hlyB protein is evident (FIG. 8A). Even in a lower stringency plot, there is little homology evident in the N-terminal amino acid sequence (FIG. 8B). However, the N-terminal region of pL28 contains transmembrane segments (FIG. 6) as does the corresponding region of the hlyB protein. Therefore, while there may be little homology in the DOTMATRIX plot because of the large number of possible hydrophobic amino acid substitutions, these regions may have functional homology. Only three single amino acid gaps are required to produce an excellent alignment (FIG. 9) of the 239 C-terminal amino acids of P-glycoprotein and the 236 C-terminal amino acids of the hlyB protein. Of the 233 possible amino acid matches produced by this alignment, 108 (46.4%) are identical and 63 (27.0%) are conserved substitutions (FIG. 9). Such extensive homology suggests these two proteins share not only a common function but also a common history.

Similarities between Multidrug Resistance and Hemolysin Export

If P-glycoprotein functions in multidrug resistance in a manner analogous to the function of the hlyB protein in hemolysin export, then it is reasonable to expect these processes to have common aspects. Both processes are affected by inhibitors of energy production and the action of local anaesthetics. When inhibitors of energy production (e.g. potassium cyanide, 2,4-dinitrophenol, sodium azide) are added to the culture medium of multidrug-resistant or drug-sensitive mammalian cells in the absence of energy sources such as glucose, the net accumulation of drug is increased. This effect is greater in multidrug-resistant cells and, if glucose is added, the intracellular levels of drug decrease more rapidly than in drug-sensitive cells. This has led to the postulation of an energy-dependent, efflux pump for drugs as the mechanism of multidrug resistance. Local anaesthetics, such as procaine, reduce the level of resistance of multidrug-resistant cells.

The export of alpha hemolysin from *E. coli* requires the molecule to traverse both the inner and outer membranes. Transport of hemolysin across the inner membrane (from the cytoplasm to the periplasmic space) is inhibited by potassium cyanide, 2,4-dinitrophenol and sodium azide and is also inhibited by procaine. In contrast, transport across the outer membrane (from the periplasmic space to the cell exterior) is not inhibited by these agents. Thus, the parallels between the effects of these inhibitors on hemolysin export and their effects on net drug accumulation and multidrug resistance supports an inner membrane location for the hlyB protein. This localization is supported by the lack of an N-terminal signal sequence in the hlyB protein and by expression of the hlyB cistron in *E. coli* minicells. The extensive homology between the amino acid sequence of P-glycoprotein and the hlyB protein, taken together with the similarities between reduced drug accumulation in multidrug-resistant mammalian cells and hemolysin transport across the inner membrane in *E. coli*, lead to inferences about the function of both molecules. All the above described effects are consistent with P-glycoprotein modulating multidrug resistance via energy-dependent drug transport across the plasma membrane and with the hlyB protein transporting hemolysin in an energydependent manner across the *E. coli* inner membrane. Strong support for these proposed roles is provided by the homology between the C-terminal regions of these proteins and another class of energy-dependent bacterial transport proteins.

Homology with Protein-Binding Dependent Bacterial Transport Systems.

A search of the NBRF Protein Sequence Database (using the FASTP program from the NBRF Protein Identification Resource) identified two bacterial transport proteins with extensive homology to the C-terminal 240 amino acids of P-glycoprotein. These were the hisP protein of the histidine permease system of S. typhimurium and the malK protein of the maltose and maltodextrin transport system of *E. coli*. Both proteins have homology with each other as well as with the pstB protein of the phosphate-specific transport system of *E. coli* and the oppD protein of the oligopeptide permease of S. typhimurium (the pstB, oppD and hlyB proteins are not in the NBRF Protein Sequence Database). These proteins are membrane-bound components of high-affinity, substrate-binding dependent, active transport systems.

Figure 10:
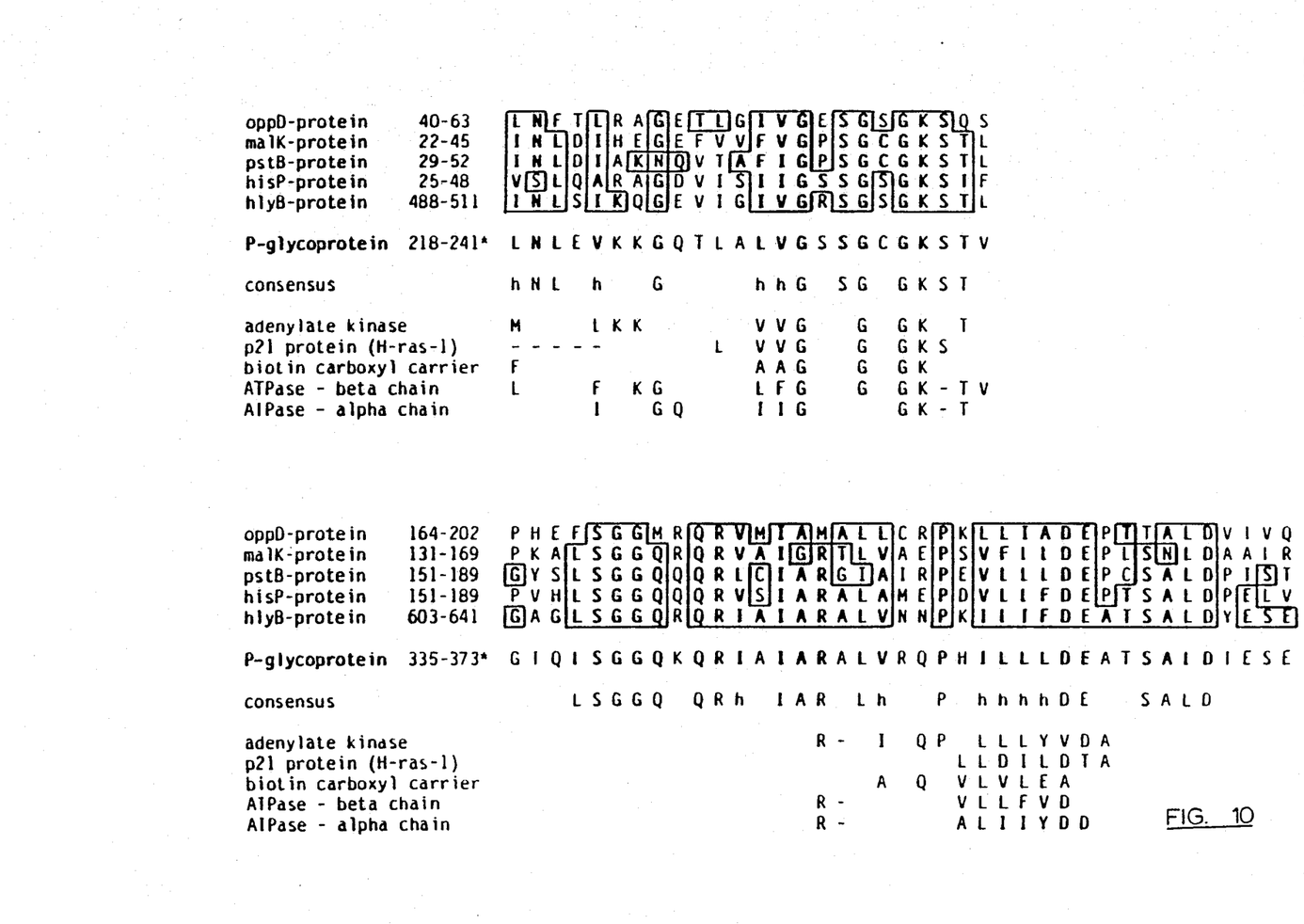
FIG. 10 shows aligned nucleotide-binding sequences of P-glycoprotein, the hemolysin B (hlyB) protein and the hisP/malK/pstB/oppD proteins. The two sequence blocks (upper and lower) correspond to the underlined regions (A—A and B—B, respectively) in FIG. 9. Amino acids are designated by their single letter code.

DOTMATRIX comparisons of the hisP/malK/pstB/oppD proteins to the C-terminal 441 amino acids of P-glycoprotein (data not shown) identified two common regions of high homology (indicated A—A and B—B in FIG. 9). These regions include sequences thought to be involved in nucleotide binding (probably ATP) that directly energizes transport. The amino acid sequences of these regions are shown in FIG. 10 along with comparable nucleotide-binding regions of five other proteins. Amino acids enclosed in boxes are either (i) identical to the corresponding amino acid in P-glycoprotein or (ii) represent highly conserved hydrophobic amino acid substitutions present in the six proteins. Amino acids in the consensus sequence represent either (i) identity between P-glycoprotein and at least four of the five bacterial protein-binding transport proteins or (ii) hydrophobic amino acid substitutions (designated by an "h") which are conserved in all six proteins but exhibit identity with P-glycoprotein in no more than three of the bacterial transport proteins.

Also shown in FIG. 10 are the comparable nucleotide binding regions of adenylate kinase (rabbit), the H-ras-1 p21 transforming protein (human), the biotin carboxyl carrier protein from Propionibacterium shermanii and the alpha and beta chains of the *E. coli* $F_1$-ATPase. These proteins were selected from known nucleotide-binding proteins because each has both of the nucleotide-binding regions present in the bacterial transport proteins and because they represent a range of functions. The amino acid sequences for these proteins were from the National Biomedical Research Foundation Protein Sequence Database. Only amino acids exhibiting identity with P-glycoprotein or with a conserved hydrophobic amino acid substitution are indicated. Other amino acids are not shown and any gaps introduced to maximize alignment (including those at the N-terminus of the p21 protein) are indicated by dashes (−).

Region A—A is characterized by the sequence hhG—G-GK. This glycine-rich region is capable of forming a flexible loop and may undergo conformational change either upon substrate binding or from interaction with another protein domain. P-glycoprotein and the five bacterial transport proteins share a more extensive sequence, hhG-SG(C/S)GKST. Additionally, they have the conserved sequence hNL-h—G which is only weakly conserved in the other nucleotide-binding proteins.

The protein sequence homology of P-glycoprotein with the five bacterial transport proteins is much greater in region B—B while, conversely, it is much less with the other nucleotide-binding proteins (FIG. 10). The feature common to this region is a hydrophobic segment of parallel $\beta$-pleated sheet followed by one or two acidic amino acids (in P-glycoprotein and the five bacterial transport proteins this has the form hhhhDE). This structure probably excludes water from the bound nucleotide in order to reduce hydrolysis. Other than in this hydrophobic segment, there is little identity between P-glycoprotein and the other nucleotide-binding proteins. However, P-glycoprotein and the five bacterial transport proteins exhibit extensive homology over 32 amino acids. This suggests that this region, in these proteins, has an important functional role in addition to nucleotide binding. Since it is the most conserved amino acid sequence among the four protein-binding dependent transport proteins, it may couple energy production directly to transport.

Figure 11:
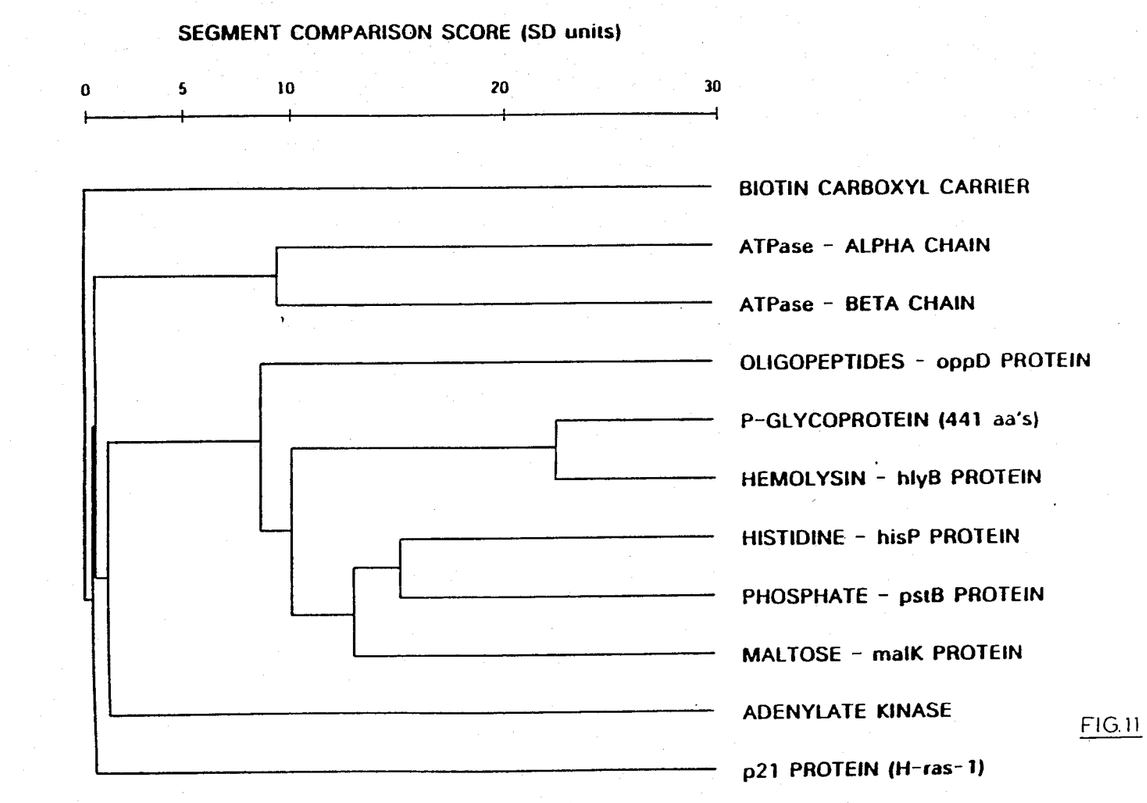
FIG. 11 shows a cluster analysis of the protein sequence homology of some nucleotide-binding proteins.

The extent of the homology between P-glycoprotein, the hlyB protein and the hisP/malK/pstB/oppD proteins and the other nucleotide-binding proteins, was determined and a cluster analysis performed to better visualize the complex interrelationships (FIG. 11). The RELATE program (from the National Biomedical Research Foundation Protein Identification Resource) was used to measure similarities between the 11 proteins whose nucleotide-binding regions are shown in FIG. 10. For each pair of proteins, the homology scores between all possible 25 amino acid segments of one protein with all possible 25 amino acid segments in the other protein were determined using the mutation probability data matrix for amino acid replacements. A numerical value derived from the distribution of scores was then determined for the actual sequences of the two proteins and for 500 runs performed using randomized sequences of both proteins. The difference between the value for the actual sequences and the mean value for the randomized runs was then divided by the standard deviation of the values from the randomized runs to yield a segment comparison score which had units of standard deviation. The probability of obtaining such a score by chance can then be estimated from a cumulative standardized normal distribution table (the probability of obtaining a score $>6$ SD is $<10^{-9}$ while the probability of a score $>10$ SD is $<10^{-23}$. Clusters were formed by merging proteins that showed the highest segment comparison scores. As clusters were formed, the score used for merging was the weighted average of the scores of the members of a cluster. The highest homology was found between P-glycoprotein and the hlyB protein. Furthermore, the cluster formed by P-glycoprotein and the hlyB protein was more similar to the hisP/malK/pstB cluster of proteins than was the oppD protein. This structural similarity suggests both P-glycoprotein and the hlyB protein function in coupling energy production to transport in a manner analogous to that in the protein-binding dependent bacterial transport proteins. The remarkable homology between P-glycoprotein and the hlyB protein further suggests that the transport of hemolysin by the hlyB protein provides the best available model for examining the role of P-glycoprotein in mediating multidrug resistance.

The discovery of the extraordinary homology between the C-terminal regions of P-glycoprotein and the hlyB protein was totally unexpected but has immediate implications for our understanding of drug resistance in cancer chemotherapy. While the homology reported here is for Chinese hamster P-glycoprotein, the conserved nature of P-glycoprotein, as detected by monoclonal antibodies and DNA hybridization, makes it virtually certain that this homology will extend to other mammalian (including human) P-glycoprotein molecules. If, as the evidence suggests, P-glycoprotein mediates multidrug resistance, it should be possible to circumvent resistance by inhibiting the function of P-glycoprotein.

The homology between P-glycoprotein and the bacterial protein-binding dependent transport proteins indicates that P-glycoprotein has a nucleotide-binding region (FIG. 10). Thus, one approach to overcoming multidrug resistance would be the use of analogues that prevent nucleotide binding by P-glycoprotein. It may be possible to exploit the homology between P-glycoprotein and the hlyB protein to screen for such analogues based on their ability to inhibit hemolysin export. In a similar manner, it may be possible to screen existing and potential anticancer agents for their differential ability to kill hemolytic and nonhemolytic bacteria. Such an approach assumes that hemolytic bacteria may be resistant to some anticancer drugs. In this regard, it is intriguing that there is a brief report that a nalidixic acid-resistant strain of E. coli had also become hemolytic (Wolton, J. R. et al, *J. Bacteriol.*, 98, 304 (1969)).

The use of calcium antagonists and calcium channel blockers to reduce the drug resistance of tumour cells is one approach currently undergoing clinical trials. It has been suggested that these compounds act not upon calcium levels in the cell but, due to their amphipathic nature, interact with the plasma membrane. Therefore, they may inhibit P-glycoprotein function in a manner similar to that by which procaine inhibits hemolysin transport across the bacterial inner membrane. This would account for the action of local anaesthetics in reducing the resistance of multidrug-resistant cells.

While the function of P-glycoprotein in drug-sensitive cells is unknown, it may be that P-glycoprotein serves to protect cells from low levels of lipophilic toxic compounds and that its role in multidrug resistance is simply an extension of this function to deal with increased levels of such compounds. Alternatively, P-glycoprotein may have a transport function unrelated to multi-drug resistance and only upon gross exaggeration of this function (e.g. by gene amplification) does resistance become apparent. If this latter is indeed the case, then the most likely candidates for transport by P-glycoprotein in drug-sensitive cells are, by analogy with hemolysin transport, large proteins. One group of potentially hemolysin-like proteins is the pore-forming molecules released by cytotoxic cells such as eosinophils, cytotoxic T lymphocytes and NK-like cells. These molecules appear to be well conserved, a finding in keeping with the conserved nature of P-glycoprotein.

The potential existence of a previously unknown protein-translocation mechanism in eukaryotic cells is perhaps the most important aspect of the homology between P-glycoprotein and the hlyB protein. The high degree of conservation of P-glycoprotein in various mammalian species suggests this protein plays a fundamental role in mammalian cells. Since P-glycoprotein appears to be encoded by a multigene family, there may be a number of homologous systems, each translocating a different protein.

We claim:

1. A monoclonal antibody specific for a conserved region located in the C-terminal portion of the P-glycoprotein cell surface antigen correlated with multidrug resistance in mammalian species, said C-terminal portion having about 239 amino acids; said antibody having cross-reactivity with P-glycoprotein cell surface antigens of different mammalian species; and said antibody being further defined by its ability to bind isolated plasma membranes of multidrug resistant cells and its inability to bind live cells; said monoclonal antibody being prepared by the process of (1) obtaining hybridomas derived by immortalizing antibody producing cells obtained from a mammal having been immunized with denatured plasma membranes obtained from mammalian cells derived from a tumor, tissue or cell line displaying multidrug resistance and (2) screening the hybridomas for production of antibody which binds isolated plasma membranes of multidrug resistant cells but does not bind live cells.

2. A monoclonal antibody as claimed in claim 1, wherein SDS denatured plasma membranes are used for immunizing a suitable mammal.

3. A monoclonal antibody as claimed in claim 1, wherein the antibody is selected by screening for the hybridomas producing antibody specific against the P-glycoprotein antigen immobilized on a solid substrate.

4. A monoclonal antibody as claimed in claim 1, wherein the antibody binds a distinct epitope in the C-terminal region of the human P-glycoprotein.

5. A monoclonal antibody specific for a conserved region located in the C-terminal portion of the P-glycoprotein cell surface antigen correlated with multidrug resistance in mammalian species, said C-terminal portion having about 239 amino acids; said antibody having cross-reactivity with P-glycoprotein cell surface antigens of different mammalian species; and said antibody being further defined by its ability to bind isolated plasma membranes of multidrug resistant cells and its inability to bind live cells.

6. A monoclonal antibody as claimed in claim 5, wherein the antibody is specific for a conserved region located in the Cterminal portion of the human P-glycoprotein.

* * * * *